United States Patent [19]

Gilbard

[11] Patent Number: 4,911,933

[45] Date of Patent: Mar. 27, 1990

[54] NON-TOXIC OPTHALMIC PREPARATIONS

[75] Inventor: Jeffrey P. Gilbard, Boston, Mass.

[73] Assignee: Eye Research Institute of Retina Foundation, Boston, Mass.

[21] Appl. No.: 232,752

[22] Filed: Aug. 16, 1988

Related U.S. Application Data

[63] Continuation of Ser. No. 915,903, Oct. 6, 1986, Pat. No. 4,775,531, which is a continuation of Ser. No. 738,953, May 29, 1985, abandoned.

[51] Int. Cl.$^4$ .................... A61K 33/14; A61K 33/06; A61K 33/10
[52] U.S. Cl. .................................. 424/663; 424/665; 424/682; 424/686; 514/769; 514/912; 514/915
[58] Field of Search ............... 424/153, 154, 127, 156, 424/663, 665, 682, 686; 514/912, 915, 769, 127

[56] References Cited

U.S. PATENT DOCUMENTS

| | | | |
|---|---|---|---|
| 2,547,653 | 4/1951 | Minnis et al. | 424/180 |
| 3,821,368 | 6/1974 | Reynolds | 424/153 |
| 3,843,782 | 10/1979 | Krezanoski et al. | 424/78 |
| 4,371,522 | 2/1983 | Gilbard | 424/153 |
| 4,443,432 | 4/1984 | Garabedian et al. | 424/153 |

OTHER PUBLICATIONS

Chem. Abst. 86:152956e (1977)–Maren.
Chem. Abst. 99:20280p (1983)–Lim et al.
Investigation Ophthamology and Visual Science, pp. 1484–1488, Nov. 1985, Bachman et al.
(International Tear Film Symposium, 9th Program and Abstracts), Nov. 7–10, 1984, Lubbock, Tex., Wilson et al.
Surv. Opthalmol. 26(2): 84–96 (1981), Haeringen.
Arvo Abstracts, May 1–6 (1983), Wilson et al.
Polack, Gainesville, Fla., Arch Ophthalmol, vol. 93, Aug. 1975, Edehauser et al.

Primary Examiner—Douglas W. Robinson
Assistant Examiner—Zohreh A. Fay
Attorney, Agent, or Firm—Lahive & Cockfield

[57] ABSTRACT

An ophthalmic preparation and a method for preparing the ophthalmic preparation is described. The ophthalmic preparation has an enhanced ability to permit essentially normal maintenance of ocular surface mucus-containing goblet cells while present in the eye.

15 Claims, 4 Drawing Sheets

NON-TOXIC OPTHALMIC PREPARATIONS

This is a continuation of application Ser. No. 915,903 now U.S. Pat. No. 4,775,531 filed Oct. 6, 1986, which is a continuation of Ser. No. 738,953, filed May 29, 1985, now abandoned.

BACKGROUND OF THE INVENTION

This invention relates to ophthalmic preparations and methods of applying the preparations to the ocular surface. More particularly, it relates to ophthalmic preparations that permit essentially normal maintenance of ocular surface mucus-containing goblet cells.

The conjunctival epithelium of the eye contains mucus-containing goblet cells. These cells secrete mucus in a controlled fashion. They thereby form a major element of the biological system by which the surface of the eye protects itself from harmful foreign matter, including but not limited to infectious agents. The goblet cells also form a critical layer of the tear film of the eye that protects the surface of the eye from dessication. Furthermore, the mucus contained within these goblet cells is a major natural lubricant for the ocular surface. The presence of a normal density of goblet cells is important for the maintenance of a healthy ocular surface.

Medicamentosa is a disease of the surface of the eye caused by the frequent administration to the eye of topical medications and/or solutions. The disease can cause ocular irritation, photophobia, conjunctival injection and keratitis. The cause of this disease has been unclear. It now has been found, however, that exposing the surface of the eye to standard ophthalmic solutions results in an accelerated loss of mucus from the conjunctival goblet cells. This loos of mucus leaves the ocular surface with an abnormally low density of mucus-containing goblet cells. This abnormal loss of goblet cell mucus is a manifestation of toxicity of the solution that was used.

It is now postulated that one mechanism responsible for the development of medicamentosa is the gradual, progressive depletion of goblet cell mucus that the exposure to standard ophthalmic solutions induces. Derangement of goblet cell mucus can decrease the eye's ability to rid itself of harmful foreign material, can engender dessication of the ocular surface, and can decrease lubrication of the surface. For example, solutions designed to lubricate the eye in fact work against that intention when they deplete the eye of goblet cell mucus—a most important natural lubricant.

It is desirable to minimize the toxicity of ophthalmic preparations. What is needed is an essentially non-toxic ophthalmic preparation which satisfies the fluid and electrolyte requirements of the ocular surface.

The composition of tear fluid has been determined to include proteins, enzymes, lipids, metabolites and electrolytes. The proteins include tear albumin, lysozyme, lactoferrin, transferrin, caeruloplasmin, immunoglobulins, complement, glycoproteins and antiproteinases. The enzymes include glycolytic enzymes and enzymes of the tricarboxlyic acid cycle, as well as lactate dehydrogenase, lysosomal enzymes, amylase, peroxidase, plasminogen activator and collagenase. The lipids include cholestrol, though lipids from other lipid classes are present. The metabolites include glucose, lactate, urea, catecholamines, histamine, and prostaglandins. The electrolytes include sodium, potassium, calcium, magnesium, chloride and bicarbonate.

It is an object of this invention to provide an ophthalmic preparation which permits essentially normal maintenance of ocular surface mucus-containing goblet cells. Another object is to provide an ophthalmic preparation which is essentially non-toxic. Another object is to provide a preparation for the improved treatment of the spectrum of dry eye disorders. Another object is to provide a preparation for selectively increasing or decreasing tear film osmolarity. Still another object is to provide a preparation of the above character which is suitable selectively for contact lens adaptation, for use as a vehicle for medicaments, and for eye comfort in general. Another object is to provide an ophthalmic preparation which may serve as an irrigation fluid and/or drug vehicle in patients with extensive lacrimal gland and/or excretory duct destruction and/or other ocular diseases where continuous or nearly-continuous ocular irrigation and/or drug therapy is desirable.

Other objects of the invention will in part be obvious and will in part appear hereinafter.

SUMMARY OF THE INVENTION

A synthetic preparation for ophthalmic use has been developed that has an enhanced ability to permit essentially normal maintenance of ocular surface mucus-containing goblet cells. The preparation leaves the conjunctiva of eyes white and non-swollen, even after prolonged bathing, e.g., for twelve hours. The preparation is non-toxic and contains a combination of electrolytes found in natural tear fluid and satisfies requirements of the ocular surface. In preferred embodiments, the synthetic preparation is substantially free of histamines. In other embodiments, the preparation is substantially free of immunoglobulins, complement, desquamated epithelial cells, bacteria and/or microorganisms.

In general, the preparation consists principally of major amounts of sodium and of chloride, and of lesser amounts of potassium and of bicarbonate. It preferably also contains other naturally-occurring elements. Other constituents may be present depending on the particular purpose of the final preparation, e.g., as a lubricating ointment, or as a medicament for the treatment of glaucoma or ocular surface infections.

The preparation typically contains between about 22.0 to 43.0 millimoles per liter (hereinafter mMoles/liter) potassium, 118.0 to 136.5 mMoles/liter chloride, 29.0 to 50 mMoles/liter bicarbonate, and 130.0 to 140.0 mMoles/liter sodium. In preferred embodiments, the potassium concentration is between about 23.0 to 42.0 mMoles/liter, the chloride concentration is between about 124.0 to 136.0 mMoles/liter, the bicarbonate concentration is between about 31.0 to 48.0 mMoles/liter, and the sodium concentration is between about 131.0 and 139.0 mMoles/liter.

While the invention is not limited thereby, it is desirable to include calcium, magnesium, and phosphate in the solution. The desirable effects of these elements on living cells are well known. See, for example, the following publications: Edelhauser et al, *Am J Ophthalmol*, 81:473, 1976; Kaye et al, *Invest Ophthalmol Vis Sci*, 7:53, 1968; Edelhauser et al, *Arch Ophthalmol*, 93:648, 1975; Edelhauser et al, *Arch Ophthalmol*, 96:516, 1978; Merrill et al, *Am J. Ophthalmol*, 49:895, 1960. The preferred concentrations are between about 0.5 to 2.0 mMoles/liter of calcium, between about 0.3 to 1.1 mMoles/liter of magnesium, and between about 0.8 to 2.2 mMoles/- liter of phosphate. More optimal is a calcium concentration between about 0.6 to 0.8 mMoles/liter, a magnesium concentration between about 0.5 to 0.6 mMoles/liter and a phosphate concentration between about 1.0 and 2.0 mMoles/liter. The preferred resulting solution has a pH value between about 7.0 and 8.0 (as measured with a Fisher pH Accumet Model 600). Nevertheless, this pH range need not be rigidly adhered to, and it may be desirable to alter pH outside of this range, for instance to improve ophthalmic drug penetration through the ocular surface. Those skilled in the art may, in view of the teachings herein, employ other pH ranges.

In preferred embodiments the preparation is isotonic. However the final osmolality may be adjusted according to the conditions present in the tear film or on the ocular surface. For example, treatment of hypertonic tear films may make diluted preparations preferable. Alternatively, the preparation may be concentrated to hypertonic concentration when therapeutically desirable such as in topical formulations for the treatment of recurrent corneal erosions. The preparations may be concentrated or diluted while minimizing undesirable properties or untoward effects of final preparation by maintaining the preferred ratios of the described electrolytes of the final ophthalmic preparations.

The preparation contains a ratio of potassium to bicarbonate in the range of 1:0.6 to 1:2.3 mMoles/liter and a preferred range of 1:.7 to 1:2.1; potassium to sodium in the range of 1:3.0 to 1:6.4 mMoles/liter and a preferred range of 1:3.1 to 1:6.0; and potassium to chloride in the range of 1:2.7 to 1:6.2 mMoles/liter and a preferred ratio of 1:2.9 to 1:5.9. In further embodiments, the preparation also contains a ratio of potassium to calcium in the range of 1:0.01 to 1:0.09 mMoles/liter and a preferred ratio of 1:0.01 to 1:0.04; potassium to magnesium in the range of 1:0.005 to 1:0.05 mMoles/liter and a preferred ratio of 1:0.01 to 1:0.03; potassium to phosphate in the range of 1:0.015 to 1:0.1 mMoles/liter and a preferred ratio of 1:0.02 to 1:0.09.

The preparation may be administered to the ocular surface by various methods. For example, the preparation may be applied topically to the ocular surface as in drops, ointments, or gels. The preparation may also be applied by means of an eye cup such that the eye is bathed. In addition, the preparation may be used with a continuous or nearly-continuous infusion device for ocular surface irrigation and/or wetting and/or drug delivery. The preparations have broad ophthalmic utility by themselves, as well as in combination with pharmaceutically and/or physically active components when it is desirable to utilize topical therapy in the eye while minimizing ocular surface toxicity.

For a fuller understanding of the nature and objects of the invention, reference should be made to the following detailed description and accompanying drawings.

DESCRIPTION OF THE INVENTION

Figure 1:
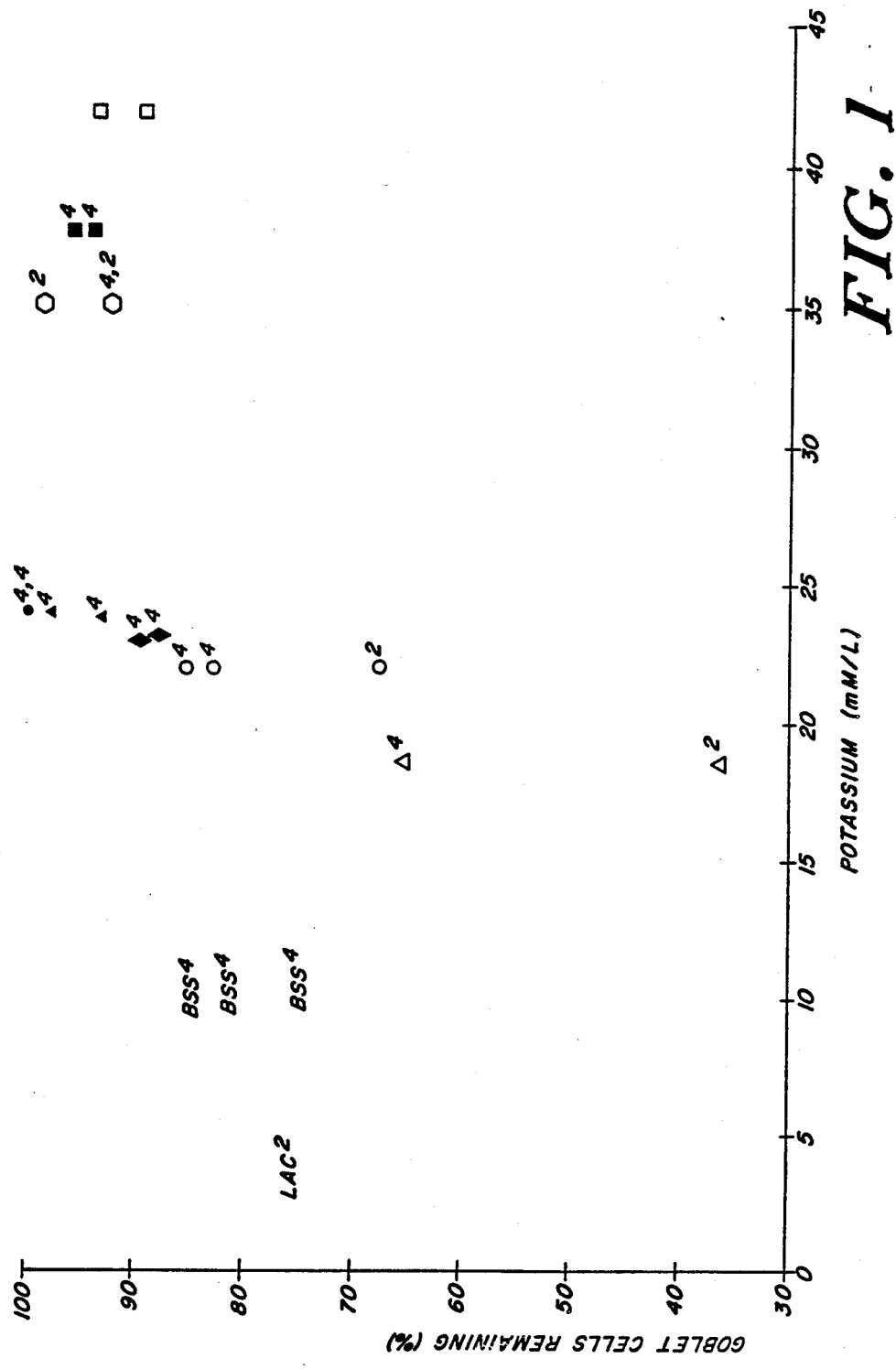
FIG. 1 shows comparative features of the invention in the form of a graph of the percentage mucus-containing goblet cells remaining after bathing for 12 hours relative to the controls as a function of potassium concentration.

In accordance with the invention, a non-toxic ophthalmic preparation combines multiple components to form a preparation which can be topically applied to the ocular surface by whichever of various methods is desired. The non-toxic ophthalmic preparation of the invention is prepared to attain between about 22.0 to 43.0 mMoles/liter of potassium, 118.0 to 136.5 mMoles/liter of chloride, 29.0 to 50.0 mMoles/liter of bicarbonate, 130.0 to 140.0 mMoles/liter of sodium, 0.5 to 2.0 mMoles/liter of calcium, 0.3 to 1.1 mMoles/liter of magnesium, and 0.8 to 2.2 mMoles/liter of phosphate.

Although it is generally desirable for the preparations to be essentially isotonic, the final osmolality or tonicity of the solution may vary. Indeed, since hypotonic and hypertonic eyedrops are brought rapidly to isotonicity by the exit or entrance, respectively, of water from the tear film, as first demonstrated by Maurice (Exp Eye Res 11, 30, 1971), and as later confirmed directly by Holly and Lamberts (Invest Ophthalmol Vis Sci 20, 236, 1981), the preferred embodiment may be diluted to hypotonic concentrations when this is therapeutically desirable. One instance occurs in the treatment of elevated tear film osmolarity, such as disclosed in U.S. Pat. No. 4,371,522. The preparation may also be concentrated to hypertonic concentrations when therapeutically desirable, such as in topical formulations for the treatment of recurrent corneal erosions.

The preferred resulting solution has a pH value between about 7.0 and 8.0 (as measured with a Fisher pH Accumet Model 600). Nevertheless, this pH range need not be rigidly adhered to, and it may be desirable to alter pH outside of this range, for instance to improve ophthalmic drug penetration through the ocular surface. Those skilled in the art may, in view of the teachings therein, employ other pH ranges.

The effect of various ophthalmic preparations on mucus-containing goblet cell density has been examined and can be further understood from the following experiments and results. It is recognized that results of tests using rabbits has close correlation with humans and therefore the results carry over to humans.

In vivo tests of various ophthalmic preparations, some according to the invention, and some according to prior art, were carried out in anesthetized rabbits. Their lids were elevated with sutures attached to elevated posts to form a conjunctival well. In separate experiments the well was filled with test solutions such that the entire ocular surface was submerged. One eye of each rabbit was bathed with a test solution, the other eye was not treated and served as a control. Baths were exchanged every hour for a twelve-hour period with fresh solution that had been bubbled with air.

At the completion of the twelve-hour period, four conjunctival biopsies were taken from the eye that had been bathed, as well as from the contralaterial control eye that had been closed for the twelve-hour period.

Biopsies were taken adjacent to the limbus with a 5 mm trephine blade in the superotemporal, superonasal, inferotemporal and inferonasal quadrants. In some experiments only two biopsies were taken from each eye. Tissue was mounted flat and stained for mucus-containing goblet cells with PAS. Goblet cells were counted in eight 0.3 square mm contiguous squares beginning immediately at the limbal margin of the biopsy and counting peripherally in the direction of the conjunctival fornices. Goblet cell densities were averaged for each eye and compared to the average density in the contralateral control eye.

Tests were run with twelve solutions, five of which are known solutions and seven of which were prepared according to the invention. The known solutions which were tested and which are further described below included Unisol TM, Balanced Salt Solution ®, Lactated Ringer's Solution, Graeme S. Wilson's Solution, and Medium 199. The solutions prepared according to the invention are Example Solutions A-G, the constituents and properties of which are further described in Table II.

The known solutions that were tested are described as follows:

(1) Unisol TM (may be obtained commercially from CooperVision) A sterile preservative-free buffered isotonic aqueous solution containing sodium chloride, boric acid and soduim borate; Osmolarity; 302 mOsm/L, (as measured with a Clifton Nanolitre Osmometer); pH:7.0. (as measured with a Fisher pH Accumet Model 600).

(2) Balanced Salt Solution ® (may be obtained commercially from Alcon Laboratories).

(3) Lactated Ringer's Solution (may be obtained commercially from Abbott Laboratories).

(4) Graeme S. Wilson's Solution (as described in the International Tear Film Symposium—1984, Lubbock, Texas).

Potassium Chloride: 18.7 mM/L
Sodium Chloride: 116.4 mM/L
Sodium Bicarbonate: 25.9 mM/L
Calcium Chloride: 0.4 mM/L
Magnesium Chloride: 0.6 mM/L
Sodium Phosphate: 0.7 mM/L (5) Medium 199 with Hank's Balanced Salt Solution and L-Glutamine modified with 1.4 g Sodium Bicarbonate per liter (may be obtained commercially from M. A. Bioproducts).

The results of tests carried out using the known solutions are indicated in Table I and the results of tests carried out using solutions prepared according to the invention are indicated in Table III.

TABLE I

Results from tests using known solutions.
(All experiments twelve-hours unless otherwise indicated)

| Solution | Percent mucus-containing goblet cells remaining | |
|---|---|---|
| Unisol | 81.1 | (2 quadrants) |
| | 71.2 | (6 hrs, 2 quadrants) |
| Lactated Ringers | 75.5 | (2 quadrants) |
| | 67.1 | (6 hrs, 2 quadrants) |
| Balanced Salt Solution | 74.9 | (2 quadrants) |
| | 81.7 | (4 quadrants) |
| | 84.9 | (4 quadrants) |
| | 93.4 | (6 hrs, 2 quadrants) |
| Wilson's Solution | 36.5 | (2 quadrants) |
| | 65.7 | (4 quadrants) |
| | 83 | (6 hrs, 2 quadrants) |
| Medium 199 | 55.5 | (2 quadrants) |
| | 76.5 | (2 quadrants) |

TABLE II

Examples Of The Invention (values expressed represent mMoles/liter.)

| Constituents | Example | | | | | | |
|---|---|---|---|---|---|---|---|
| | A | B | C | D | E | F | G |
| Potassium chloride | 22.0 | 42.0 | 35.0 | 24.0 | 38.0 | 23.0 | 24.0 |
| Calcium chloride | 0.8 | 0.8 | 0.8 | 0.8 | 0.6 | 0.8 | 0 |
| Magnesium chloride | 0.6 | 0.6 | 0.6 | 0.6 | 0.5 | 0.6 | 0 |
| Sodium phosphate | 1.0 | 2.0 | 1.0 | 1.0 | 1.0 | 1.0 | 0 |
| Sodium bicarbonate | 29.20 | 47.2 | 35.0 | 32.0 | 40.0 | 31.0 | 32.0 |
| Sodium chloride | 109.80 | 89.80 | 98.0 | 99.0 | 90 | 102.0 | 100.0 |
| pH, (as measured with a Fisher pH-Accument Model 600) | 7.3 | 7.4 | 7.2 | 7.4 | 7.5 | 7.4 | 7.4 |
| Osmolality, (as measured with a Clifton Nanoliter Osmometer; milliosmoles per Kg.) | 296 | 325 | 304 | 302 | 306 | 301 | 296 |

*Brought to pH 7.4 by adding 1 molar HCL

TABLE III

Results (twelve hrs. unless otherwise noted)

| Example | Percent Mucus-Containing Goblet Cells Remaining | |
|---|---|---|
| A | 67.5 | (2 quadrants) |
| | 85 | (4 quadrants) |
| | 82.3 | (4 quadrants) |
| | 98 | (6 hrs, 2 quadrants) |
| B | 93.5 | (2 quadrants) |
| | 89.4 | (2 quadrants) |
| C | 98.55 | (2 quadrants) |
| | 91.4 | (2 quadrants) |
| | 91.6 | (4 quadrants) |
| D | 99.3 | (4 quadrants) |
| | 99.4 | (4 quadrants) |
| E | 95.6 | (4 quadrants) |
| | 94.4 | (4 quadrants) |
| F | 88.3 | (4 quadrants) |
| | 89.7 | (4 quadrants) |
| G | 98.25 | (4 quadrants) |
| | 93.37 | (4 quadrants) |

As indicated in Tables I and III, the solutions prepared according to the invention attained a higher percentage of mucus-containing goblet cells remaining as compared to the known solutions. The high percentage of goblet cells remaining indicates the non-toxicity and normal maintenance of the ocular surface achieved by Solutions A-G.

The percentage mucus-containing goblet cells remaining is high not only for solutions A-F, which contain potassium, chloride, calcium, magnesium, sodium phosphate and bicarbonate, but is also high for solution G, which contains only potassium, chloride, sodium and bicarbonate.

Figure 2:
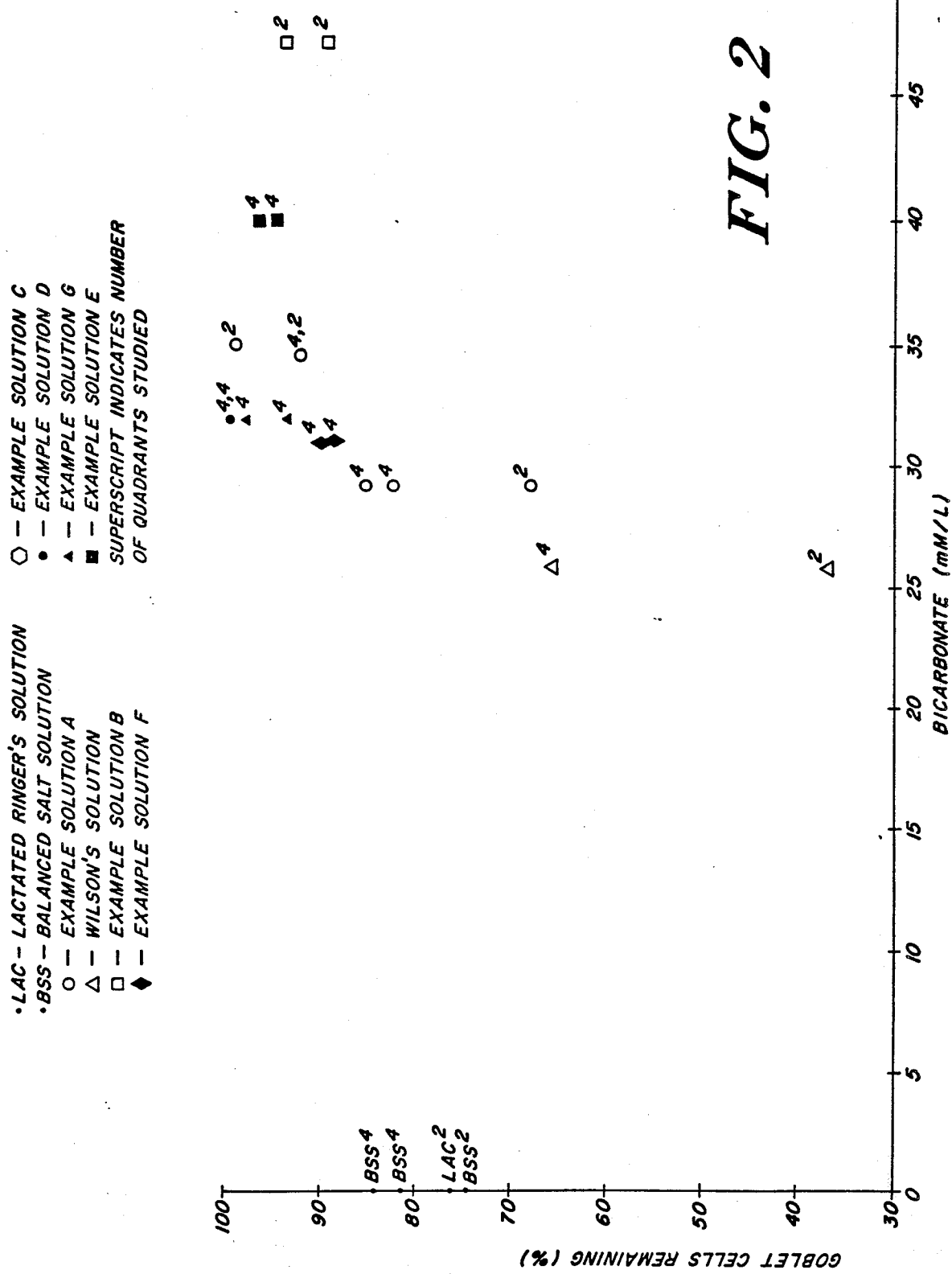
FIG. 2 shows comparative features of the invention in the form of a graph of the percentage mucus-containing goblet cells remaining after bathing for 12 hours relative to the controls as a function of bicarbonate concentration.
Figure 3:
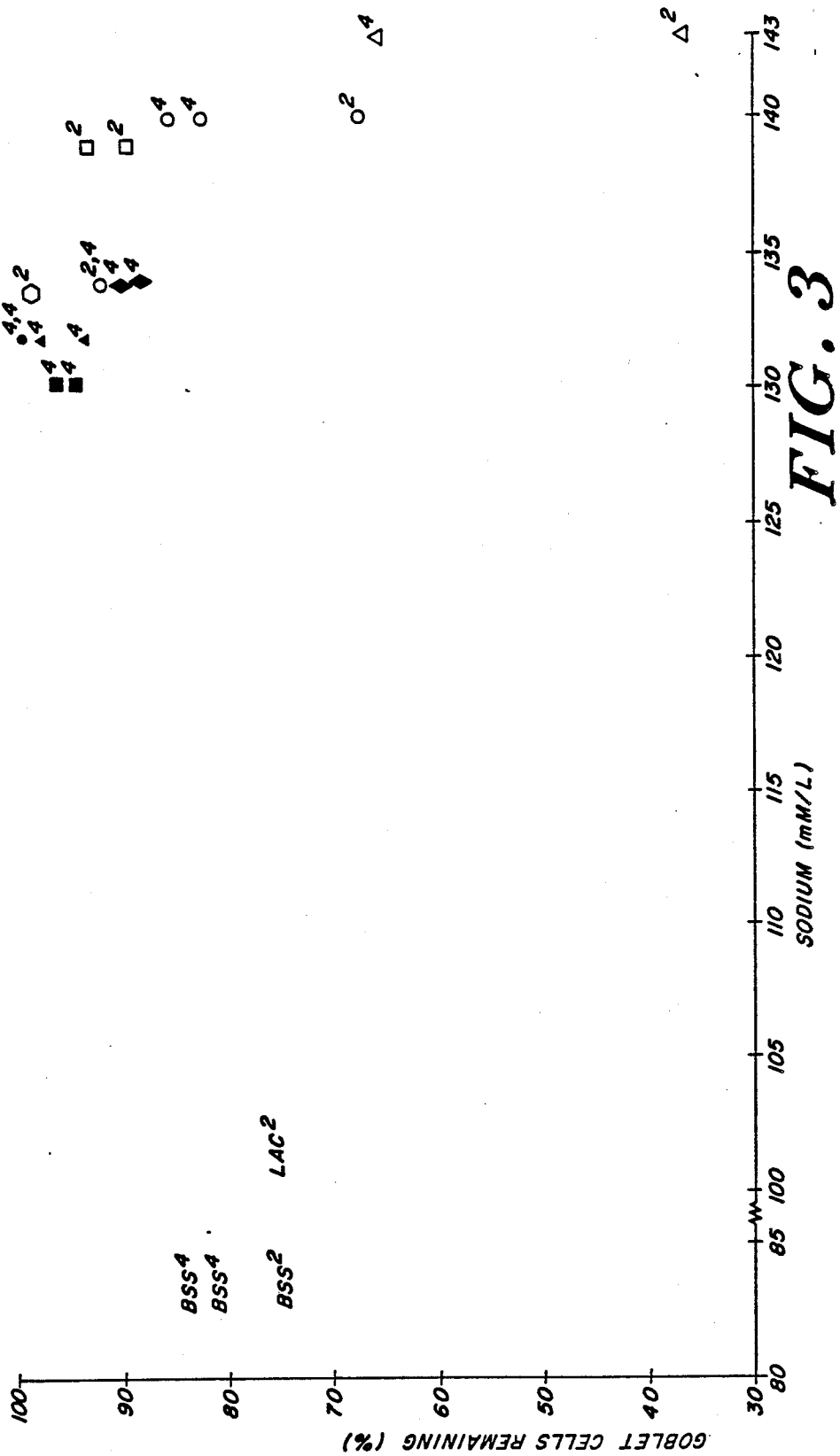
FIG. 3 shows comparative features of the invention in the form of a graph of the percentage mucus-containing goblet cells remaining after bathing for 12 hours relative to the controls as a function of sodium concentration.
Figure 4:
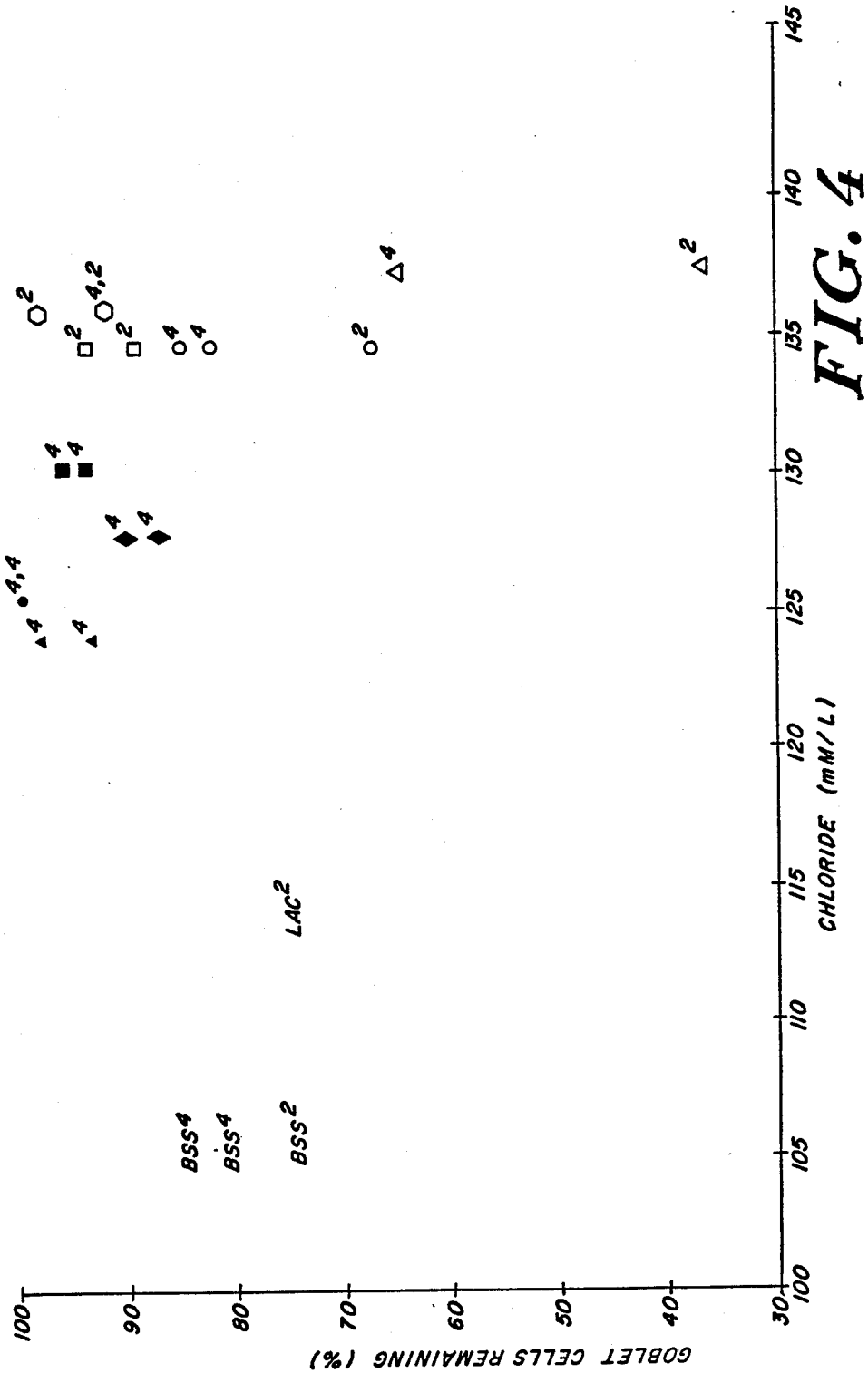
FIG. 4 shows comparative features of the invention in the form of a graph of the percentage mucus-containing goblet cells remaining after bathing for 12 hours relative to the controls as a function of chloride concentration.

The results from tests carried out using the various known and Example Solutions are also indicated in FIGS. 1-4. The figures demonstrate the percent of mucus-containing goblet cells remaining as a function of the concentration of particular constituents in the various solutions. As can be seen in the Figures, varying the concentrations of the constituents significantly affects the percentage of mucus-containing goblet cells remaining.

While the invention is not limited thereby, the described ophthalmic preparations can be used as an artificial tear solution, as an ocular wetting solution, as a drug vehicle, as a solution for increasing eye comfort, as a contact lens wetting solution, as well as a contact lens soaking solution. The preparations can be administered to the eye according to conventional practices, including topically as a drop, in an ointment, and as a gel. It can also be applied to the eye via an eye cup, or infused into the tear film on a continuous or nearly continuous basis with a pump and catheter type of system.

It will thus be seen that the objects set forth above, among those made apparent from the preceding description, are efficiently attained and, since certain changes may be made in formulating the above preparations without departing from the scope of the invention, it is intended that all matter contained in the above description shall be interpreted as illustrative and not in a limiting sense.

What is claimed is:

1. The method of wetting contact lenses before insertion into the eye which reduces or eliminates damage to the eye caused by the wetting solution comprising the step of applying to said contact lens a non-irritating solution, or a therapeutically effective dilution of said solution, before insertion, wherein said non-irritating solution contains potassium, chloride, bicarbonate, and sodium as essential ingredients and is characterized in that:
   (a) said potassium concentration is about 22.0 to 43.0 mM/l,
   (b) said bicarbonate concentration is about 29.0 to 50.0 mM/l,
   (c) said sodium concentration is about 130.0 to 140.0 mM/l, and
   (d) said chloride concentration is about 118.0 to 136.5 mM/l,
   whereby said solution has an osmolality of about 296-325 mOsm/Kg.

2. The method of claim 1 whereby said non-irritating solution further comprises calcium, magnesium, and phosphate as essential ingredients and is characterized in that:
   (a) said calcium concentration is about 0.5 to 2.0 mM/l,
   (b) said magnesium concentration is about 0.3 to 1.1 mM/l, and
   (c) said phosphate concentration is about 0.8 to 2.2 mM/l.

3. The method of claim 2 wherein said non-irritating solution is characterized in that:
   (a) said potassium concentration is about 23.0 to 42.0 mM/l,
   (b) said bicarbonate concentration is about 31.0 to 48.0 mM/l,
   (c) said sodium concentration is about 131.0 to 139.0 mM/l,
   (d) said chloride concentration is about 124.0 to 136.0 mM/l,
   (e) said calcium concentration is about 0.6 to 0.8 mM/l,
   (f) said magnesium concentration is about 0.5 to 0.6 mM/l, and
   (g) said phosphate concentration is about 1.8 to 2.0 mM/l.

4. A method of delivering drugs to the ocular surface of humans and animals comprising the steps of suspending or dissolving said drug in a non-toxic drug delivery vehicle, or a therapeutically effective dilution of said vehicle, and applying said drug to the ocular surface of in the eye said vehicle, wherein said vehicle contains potassium, chloride, bicarbonate, and sodium as essential ingredients and is characterized in that:
   (a) said potassium concentration is about 22.0 to 43.0 mM/l,
   (b) said bicarbonate concentration is about 29.0 to 50.0 mM/l,
   (c) said sodium concentration is about 130.0 to 140.0 mM/l, and
   (d) said chloride concentration is about 118.0 to 136.5 mM/l,
   whereby said solution has an osmolality of about 296-325 mOsm/Kg.

5. The method of claim 4 whereby said drug delivery vehicle further comprises calcium, magnesium, and phosphate as essential ingredients and is characterized in that:
   (a) said calcium concentration is about 0.5 to 2.0 mM/l,
   (b) said magnesium concentration is about 0.3 to 1.1 mM/l, and
   (c) said phosphate concentration is about 0.8 to 2.2 mM/l.

6. The method of claim 5 wherein said drug delivery vehicle is characterized in that:
   (a) said potassium concentration is about 23.0 to 42.0 mM/l,
   (b) said bicarbonate concentration is about 31.0 to 48.0 mM/l,
   (c) said sodium concentration is about 131.0 to 139.0 mM/l,
   (d) said chloride concentration is about 124.0 to 136.0 mM/l,
   (e) said calcium concentration is about 0.6 to 0.8 mM/l,
   (f) said magnesium concentration is about 0.5 to 0.6 mM/l, and
   (g) said phosphate concentration is about 1.8 to 2.0 mM/l.

7. A method of lubricating the ocular surface of contact lens wearers comprising the step of topical administration of an ocular lubricant, or a therapeutically effective dilution of said lubricant, to the ocular surface, wherein said ocular lubricant contains potassium, chloride, bicarbonate, and sodium as essential ingredients and is characterized in that:
   (a) said potassium concentration is about 22.0 to 43.0 mM/l,
   (b) said bicarbonate concentration is about 29.0 to 50.0 mM/l,
   (c) said sodium concentration is about 130.0 to 140.0 mM/l, and
   (d) said chloride concentration is about 118.0 to 136.5 mM/l, whereby said solution has an osmolality of about 296–325 mOsm/Kg.

8. The method of claim 7 whereby said ocular lubricant further comprises calcium, magnesium, and phosphate as essential ingredients and is characterized in that:
 (a) said calcium concentration is about 0.5 to 2.0 mM/l,
 (b) said magnesium concentration is about 0.3 to 1.1 mM/l, and
 (c) said phosphate concentration is about 0.8 to 2.2 mM/l.

9. The method of claim 8 wherein said ocular lubricant is characterized in that:
 (a) said potassium concentration is about 23.0 to 42.0 mM/l,
 (b) said bicarbonate concentration is about 31.0 to 48.0 mM/l,
 (c) said sodium concentration is about 131.0 to 139.0 mM/l,
 (d) said chloride concentration is about 124.0 to 136.0 mM/l,
 (e) said calcium concentration is about 0.6 to 0.8 mM/l,
 (f) said magnesium concentration is about 0.5 to 0.6 mM/l, and
 (g) said phosphate concentration is about 1.8 to 2.0 mM/l.

10. A method of increasing eye comfort comprising the step of topical administration of an eye drop, or a therapeutically effective dilution of said eye drop, to the ocular surface, wherein said eye drop contains potassium, chloride, bicarbonate, and sodium as essential ingredients and is characterized in that:
 (a) said potassium concentration is about 22.0 to 43.0 mM/l,
 (b) said bicarbonate concentration is about 29.0 to 50.0 mM/l,
 (c) said sodium concentration is about 130.0 to 140.0 mM/l, and
 (d) said chloride concentration is about 118.0 to 136.5 mM/l,
whereby said eye drop has an osmolality of about 296–325 mOsm/kg.

11. The method of claim 10 whereby said eye drop further comprises calcium, magnesium, and phosphate as essential ingredients and is characterized in that:
 (a) said calcium concentration is about 0.5 to 2.0 mM/l,
 (b) said magnesium concentration is about 0.3 to 1.1 mM/l, and
 (c) said phosphate concentration is about 0.8 to 2.2 mM/l.

12. The method of claim 11 wherein said eye drop is characterized in that:
 (a) said potassium concentration is about 23.0 to 42.0 mM/l,
 (b) said bicarbonate concentration is about 31.0 to 48.0 mM/l,
 (c) said sodium concentration is about 131.0 to 139.0 mM/l,
 (d) said chloride concentration is about 124.0 to 136.0 mM/l,
 (e) said calcium concentration is about 0.6 to 0.8 mM/l,
 (f) said magnesium concentration is about 0.5 to 0.6 mM/l, and
 (6) said phosphate concentration is about 1.8 to 2.0 mM/l.

13. The method of keeping contact lenses moist when out of the eye comprising the step of immersing said contact lens in a soaking solution, or a therapeutically effective dilution of said solution, before insertion, wherein said soaking solution contains potassium, chloride, bicarbonate, and sodium as essential ingredients and is characterized in that:
 (a) said potassium concentration is about 22.0 to 43.0 mM/l,
 (b) said bicarbonate concentration is about 29.0 to 50.0 mM/l,
 (c) said sodium concentration is about 130.0 to 140.0 mM/l, and
 (d) said chloride concentration is about 118.0 to 136.5 mM/l,
whereby said solution has an osmolality of about 296–325 mOsm/Kg.

14. The method of claim 13 whereby said soaking solution further comprises calcium, magnesium, and phosphate as essential ingredients and is characterized in that:
 (a) said calcium concentration is about 0.5 to 2.0 mM/l,
 (b) said magnesium concentration is about 0.3 to 1.1 mM/l, and
 (c) said phosphate concentration is about 0.8 to 2.2 mM/l.

15. The method of claim 14 wherein said soaking solution is characterized in that:
 (a) said potassium concentration is about 23.0 to 42.0 mM/l,
 (b) said bicarbonate concentration is about 31.0 to 48.0 mM/l,
 (c) said sodium concentration is about 131.0 to 139.0 mM/l,
 (d) said chloride concentration is about 124.0 to 136.0 mM/l,
 (e) said calcium concentration is about 0.6 to 0.8 mM/l,
 (f) said magnesium concentration is about 0.5 to 0.6 mM/l, and
 (g) said phosphate concentration is about 1.8 to 2.0 mM/l.

* * * * *

UNITED STATES PATENT AND TRADEMARK OFFICE
CERTIFICATE OF CORRECTION

PATENT NO. : 4,911,933
DATED : March 27, 1990
INVENTOR(S) : Gilbard, Jeffrey

It is certified that error appears in the above-identified patent and that said Letters Patent is hereby corrected as shown below:

Column 1,
Line 3, the following two sentences should be inserted:

-- Statement of Rights
This invention was made with government support under Grant EY33703 awarded by the National Institutes of Health. The Government has certain rights in the invention. --

Signed and Sealed this

Fourteenth Day of October, 2003

JAMES E. ROGAN
*Director of the United States Patent and Trademark Office*